United States Patent
Hall et al.

[11] 3,959,289
[45] May 25, 1976

[54] DERIVATIVES OF 4,6 DIOXOPYRIDO[3,2-G]QUINOLINE 2,8 DICARBOXYLIC ACID

[75] Inventors: Charles M. Hall; Herbert G. Johnson; John B. Wright, all of Kalamazoo, Mich.

[73] Assignee: The Upjohn Company, Kalamazoo, Mich.

[22] Filed: Dec. 11, 1974

[21] Appl. No.: 531,759

Related U.S. Application Data

[60] Division of Ser. No. 303,971, Nov. 6, 1972, which is a continuation-in-part of Ser. No. 233,772, March 10, 1972, abandoned, which is a continuation-in-part of Ser. No. 230,034, Feb. 28, 1972, abandoned.

[52] U.S. Cl. ............... 260/287 CF; 260/268 BQ; 260/286 R; 260/286 Q; 260/471 A; 424/258
[51] Int. Cl.² .................................. C07D 471/04
[58] Field of Search ........................ 260/287 CF

[56] References Cited
UNITED STATES PATENTS
3,790,577   2/1974   Waring .......................... 260/287 R

*Primary Examiner*—Alton D. Rollins
*Assistant Examiner*—David E. Wheeler
*Attorney, Agent, or Firm*—Martin B. Barancik; Roman Saliwanchik

[57] ABSTRACT

Novel chemical compounds of the formula:

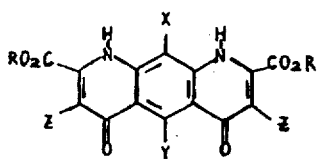

wherein
R is selected from the group consisting of hydrogen, alkyl from one to three carbon atoms, inclusive, phenyl, alkali metal, or an amine cation;
X and Y can be the same or different and are selected from the group consisting of hydrogen, alkyl of from one to six carbon atoms, inclusive, cycloalkyl of 5 or 6 carbon atoms, inclusive, phenyl, hydroxyl, alkoxy having from one to three carbon atoms, inclusive, halogen, trifluoromethyl, cyano, carboxyamide and O C-OQ,

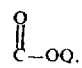

where
Q is selected from the group consisting of hydrogen, alkyl from one to three carbon atoms, inclusive, alkali metal, and an amine cation, with the proviso that where
R is hydrogen, alkali metal or an amine cation, then Q is the same as R, and where
R is phenyl or alkyl from one to three carbon atoms, then Q is phenyl or alkyl from one to three carbon atoms; and
Z is selected from the group consisting of hydrogen, alkyl from one to three carbon atoms, inclusive, and phenyl.

The compounds are formulated with pharmaceutical carriers for oral or parenteral administration, with insufflation being the preferred method. The compositions are useful in the prophylactic treatment of sensitized humans and mammals for allergy and all anaphylactic reactions of a reagin or non-reagin mediated nature.

6 Claims, No Drawings

DERIVATIVES OF 4,6 DIOXOPYRIDO[3,2-G]QUINOLINE 2,8 DICARBOXYLIC ACID

CROSS REFERENCE TO RELATED APPLICATIONS

This application is a divisional of co-pending application Ser. No. 303,971, filed Nov. 6, 1972, which is a continuation-in-part application of our copending application, Ser. No. 233,772, filed on Mar. 10, 1972, now abandoned, which is a continuation-in-part application of our copending application, Ser. No. 230,034, filed on Feb. 28, 1972 now abandoned.

BRIEF SUMMARY OF THE INVENTION

This invention relates to novel compounds, pharmaceutical compositions and a process for the prophylactic treatment of allergic conditions.

DETAILED DESCRIPTION OF THE INVENTION

In accordance with this invention, we provide compounds represented by structure 1a

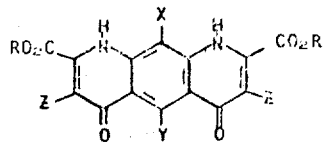

(1a)

wherein it is understood that 1a can exist in its tautomeric form 1b and that the compounds of this invention are likely to be mixtures of all tautomeric forms, the percentages of each tautomer to be at least partially dependent on the nature of R, X, Y, and Z and the physical environment of the compound.

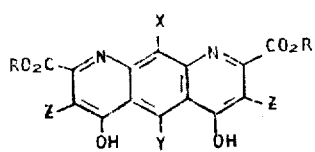

(1b)

For the purpose of brevity throughout the application and appended claims, the compounds will be referred to hereinafter in their keto form, structure 1a.

The R substituent is selected from the group consisting of hydrogen, alkyl from one to three carbon atoms, inclusive, phenyl, alkali metal, or an amine cation, the amine selected from the group consisting of ammonia tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2,-2',2''-nitrilotriethanol; X and Y can be the same or different and are selected from the group consisting of hydrogen, alkyl of from one to six carbon atoms, inclusive, cycloalkyl of 5 or 6 carbon atoms, inclusive, phenyl, hydroxyl, alkoxy having from one to three carbon atoms, inclusive, halogen, trifluoromethyl, cyano, carboxyamide and

where Q is selected from the group consisting of hydrogen, alkyl from one to three carbon atoms, inclusive, alkali metal, and an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2', 2''-nitrilotriethanol with the proviso that where R is hydrogen, alkali metal or an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2', 2''-nitrilotriethanol, Q is the same as R, and that where R is phenyl or alkyl from one to three carbon atoms, then Q is phenyl or alkyl from one to three carbon atoms. The Z substituent is selected from the group consisting of hydrogen, alkyl from one to three carbon atoms, inclusive, and phenyl.

The preferred compounds are those compounds where R is selected from the group consisting of hydrogen, alkali metals and an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2', 2''-nitrilotriethanol X and Y are the same or different and are selected from the group consisting of hydrogen, alkyl from one to three carbon atoms, inclusive, phenyl, hydroxyl, halogen, alkoxy having from one to three carbon atoms, inclusive, trifluoromethyl, cyano, carboxyamide and

where Q is selected from the group consisting of hydrogen, alkali metal, and an amine cation, the amine selected from the group consisting of ammonia, tri(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2', 2''-nitrilotriethanol with the proviso that Q is the same as R. Z is selected from the group consisting of hydrogen and alkyl from one to three carbon atoms, inclusive.

The more preferred compounds are those compounds where R is selected from the group consisting of alkali metal and an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis-(hydroxymethyl)-2, 2', 2''-nitrilotriethanol; X and Y can be the same or different and are selected from the group consisting of alkyl from one to three carbon atoms, inclusive, alkoxy having one to three carbon atoms, inclusive, halogen, cyano,

where Q is selected from the group consisting of alkali metal and an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2′, 2″-nitrilotriethanol with the proviso that Q is the same as R. Y is hydrogen. Z is hydrogen.

The most preferred compounds are those compounds

The compounds of this invention can be prepared by methods known to the art. The basic synthetic pathway employed is the reaction of an appropriately substituted m-diaminobenzene (II) with an oxaloacetate sodium salt (III) in the presence of a solvent to form the diadduct (IV). The R group is limited to the alkyl group of from one to three carbon atoms, inclusive, and phenyl. Ring closure to the desired compound (Ia) is accomplished by heating the diadduct at appropriate conditions.

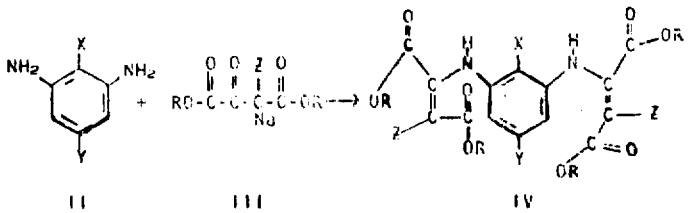

where R is an alkali metal or an amine cation, the amine selected from the group consisting of ammonia, cris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2′, 2″-nitrilotriethanol; X is selected from the group consisting of fluoro, chloro, methyl, ethyl, cyano, methoxy, ethoxy, and

where Q is selected from the group consisting of alkali metal and an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2′, 2″-nitrilotriethanol, with the proviso that Q is the same as R, and Y is selected from the group consisting of hydrogen, methyl, nitrile, and

where Q is selected from the group consisting of alkali metal, and an amine cation, the amine selected from the group consisting of ammonia, tris(hydroxymethyl)aminomethane, D-threo-2-amino-1-nitrophenyl-1,3-propanediol, N,N-bis(hydroxyethyl)-piperazine, 2-amino-2-methyl-1-propanol-2-amino-2-methyl-1,3-propanediol and 2,2-bis(hydroxymethyl)-2, 2′, 2″-nitrilotriethanol with the proviso that Q is the same as R; and Z is hydrogen.

As employed in the above disclosure and throughout the specification, the term "halogen" includes fluoro, chloro, bromo, and iodo and the term "alkyl" includes methyl, ethyl, propyl, and isopropyl when limited to three carbon atoms and includes butyl, isobutyl, tertbutyl, pentyl, isopentyl, neopentyl, hexyl, isohexyl, and 3-dimethylbutane when limited to six carbon atoms. "Alkali metal" includes sodium and potassium.

After the above synthesis has been carried out, the carboxylate can be transesterified to other esters or hydrolyzed to the carboxy acid. The carboxy acid is converted to the alkali metal or amine salts by standard methods.

X and Y substituted meta diaminobenzene starting materials have been prepared in the art prior to this invention. Furthermore, a substantial number of X and Y substituted m-dinitrobenzenes are known. These nitro groups can be easily reduced to amino groups by various methods including the use of iron and acetic acid, catalytic hydrogenation in the presence of platinum or palladium, or stannous chloride and concentrated hydrochloric acid.

Included among starting materials made available by the art are the following substituted benzene compounds:

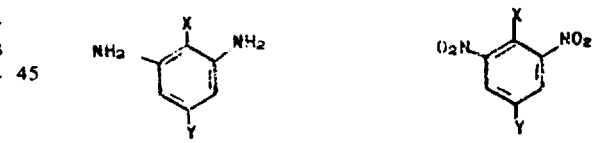

TABLE I

| X | Y | X | Y |
|---|---|---|---|
| CH₃ | H | C₂H₅ | H |
| Cl | H | OH | H |
| OCH₃ | H | CH₃ | COOH |
| OC₂H₅ | H | Cl | CH₃ |
| CH₃ | CH₃ | Cl | COOH |
| Cl | CH₃ | COOH | H |
| C₆H₅ | H | CN | H |
|   |   | F | H |
|   |   | Br | H |
|   |   | I | H |
|   |   | OC₂H₅ | CH₃ |
|   |   | C₃H₇ | H |
|   |   | OC₃H₇ | H |
|   |   | H | OCH₃ |
|   |   | H | C-NH₂ (O) |
|   |   | H | CN |
|   |   | OH | OH |
|   |   | H |   |
|   |   | CH₃ | COOH |
|   |   | CH₃ | CH₃ |

TABLE I-continued

| X | Y | X | Y |
|---|---|---|---|
| | | $CH_3$ | $OC_2H_5$ |
| | | OH | $C_3H_7$ |
| | | OH | |
| | | H | $C_3H_7$ |
| | | $C_2H_5$ | $CH_3$ |
| | | $CH_3$ | $C_2H_5$ |

Other diamino starting materials are readily synthesized from available compounds. For example, o-dinitrotrimethylfluorobenzene is prepared by reacting o-dinitrobenzoic acid with sulfur tetrafluoride.

The second reactant, the oxaloacetate derivative is also readily available. Compounds where R is ethyl and Z is hydrogen, ethyl or phenyl are known in the art and isopropyl is easily prepared.

Where Z is hydrogen, an alternative reagent to the oxaloacetate derivative is available to form the diadduct. Acetylene dicarboxylate (V), where R is limited to alkyl of from one to three carbon atoms, inclusive, or phenyl, can be added to the diaminobenzene derivative to form the diadduct (IV) as illustrated below:

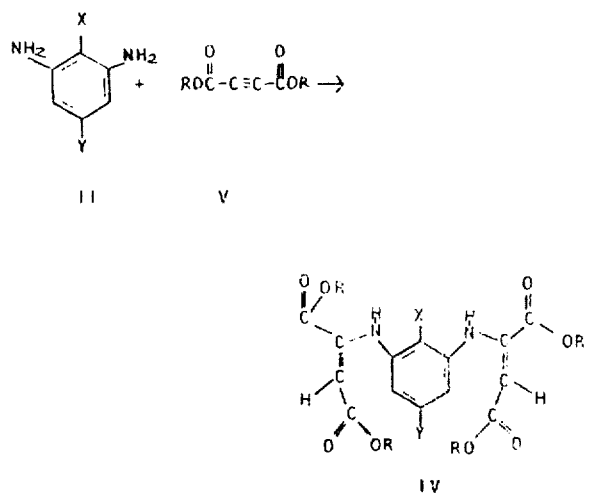

In the formation of the diadduct and subsequent ring closure, the following processing conditions can be observed.

When using the oxaloacetate reagent to form the diadduct, there should be a sufficient amount of acid present to protonate the oxaloacetate carbanion and catalyze the removal of the keto grouping as water. The acid can also serve as a solvent for the two reagents as well. For example, glacial acetic acid, propionic acid, p-toluene sulfonic acid, and butyric acid are acids which can be used. If a further reagent is needed to place the two reactants into solution, (or a cosolvent desired), benzene, toluene, diethyl ether, dioxane, tetrahydrofuran, or alcohols from one to about four carbon atoms can be employed. The length of time for the formation of the diadduct is temperature dependent. At room temperature the reaction proceeds rather slowly but as the temperature is raised, reaction time is decreased. Acceptable reaction times are achieved at temperatures ranging from about 40° to about 70° C., although reaction temperatures can be above 100° C. if desired.

With regard to the use of the acetylene dicarboxylate reactant in the formation of the diadduct, appropriate solvents are alcohols having from one to about six carbon atoms, preferably one to about three carbon atoms, benzene, diethylether, dioxane, tetrahydrofuran, or any other solvent which places both of the reactants in solution and allows the desired compound to form. Generally the reaction proceeds readily at room temperature and can be promoted by an increase in temperature to about 100° C.

Ring closure of the diadduct, prepared by the methods disclosed above, and formation of the desired compound can be accomplished by heating the diadduct at a relatively high temperature. This heating can be done to the neat diadduct. However, it is preferred to use a solvent which can function as a heat transfer medium. Any high boiling inert solvent such as a mineral oil, hexamethylphosphoric triamide, diphenyl ether, or Dowtherm A, which appears to be primarily a diphenyl ether side product of the Dow Chemical Company preparation of phenol, is suitable. The ring cyclization step is preferably carried out at temperatures of from about 220° to about 280° C., although lower or higher temperatures can be employed if desired. A particularly preferred solvent is Dowtherm A, which boils at 250° C., thus enabling the ring cyclization to occur during reflux.

An additional advantage of the elevated temperature during the ring cyclization step is that any adduct formed in the preceding step which is not in a position to cyclize since it is trans to the benzene ring is isomerized to the cis configuration during heating, thereby allowing substantial yields of the desired compound to be produced. This trans adduct preparation occurs more frequently when a non-polar solvent and acetylene dicarboxylate are used in the adduct formation step.

The desired compound is isolated and crystallized by conventional methods. Isomers of the desired product are generally insignificant. However, when X and Y are both hydrogen or X is hydrogen and Y can be certain groups such as methyl, chlorine, or cyano, ring cyclization can possibly occur at the X position as well as at the desired positions. However, these isomeric mixtures can be resolved using standard techniques. For example, where X is hydrogen, an isomeric mixture can be readily separated using silica gel or alumina as the chromatographic support and a mixture of methylene chloride and methanol as the eluant. In cases wherein the desired compound is prepared in very poor yield or the mixture compounds are difficult to separate, an alternate route for the preparation of the desired compound is the preparation of a compound wherein X is halogen, preferably chlorine, followed by hydrogenation over a palladium/charcoal catalyst. This treatment replaces the halogen with hydrogen, thereby preparing the compound which is desired.

As stated previously, at this point various esters, the acid, or salts can be prepared at the R position of the carboxy group. Different esters can be prepared by standard transesterification reaction. Ester groups are converted to the acid by treatment with base and acid. The acid can then be easily converted to the amine or alkali metal salts by contacting the diacid with two equivalents of the desired amine or alkali metal and heating in a sufficient amount of water to effect solubilization. The crystalline salts can be precipitated by the addition of methanol. When R is hydrogen, alkali metal, or amine cation, and X or Y is COOQ, then Q is the same as R.

Following is an illustrative list of reactants and desired compounds which can be prepared by the above disclosed procedures:

TABLE II

| Starting Materials | | Product |
|---|---|---|

$H_2N$-[ring]-$NH_2$ + $RO-C-C\equiv C-C-OR$ or $RO-C-C-C-C-OR$ (Na)  →  [quinoline product]

| X | Y | R |
|---|---|---|
| H | H | $CH_3$ |
| H | $CH_3$ | $CH_3$ |
| H | $C_2H_5$ | $CH_3$ |
| H | $iC_3H_7$ | $CH_3$ |
| H | $iC_4H_9$ | $CH_3$ |
| H | $iC_5H_{11}$ | $CH_3$ |
| H | 2,3-dimethylbutane | $CH_3$ |
| $iC_3H_7$ | H | $CH_3$ |
| $CH_3$ | $CH_3$ | $CH_3$ |
| $C_2H_5$ | $tC_4H_9$ | $CH_3$ |
| neopentyl | $C_3H_7$ | $CH_3$ |
| $nC_6H_{13}$ | $C_2H_5$ | $C_2H_5$ |
| $iC_3H_7$ | $C_5H_9$ | $C_2H_5$ |
| $C_4H_{11}$ | $C_2H_5$ | $C_2H_5$ |
| $C_6H_5$ | OH | $C_2H_5$ |
| OH | $iC_3H_7$ | $C_2H_5$ |
| OH | OH | $C_2H_5$ |
| OH | H | $C_2H_5$ |
| OH | $OC_2H_5$ | $C_2H_5$ |
| $OiC_3H_7$ | OH | $C_2H_5$ |
| OH | Br | $C_2H_5$ |
| OH | $CF_3$ | $C_2H_5$ |
| CN | OH | $C_3H_7$ |
| OH | $iC_5H_{11}$ | $C_3H_7$ |
| OH | $C_3H_7$ | $C_3H_7$ |
| $CONH_2$ | OH | $C_3H_7$ |
| OH | $COOC_2H_5$ | $C_3H_7$ |
| $COOCH_3$ | OH | $C_3H_7$ |
| $C_2H_5$ | $C_6H_5$ | $C_3H_7$ |
| $OCH_3$ | F | $C_3H_7$ |
| I | $OC_2H_5$ | $C_3H_7$ |
| $OC_3H_7$ | $CF_3$ | $C_3H_7$ |
| CN | $OiC_3H_7$ | $C_3H_7$ |
| $OC_2H_5$ | $CONH_2$ | $iC_3H_7$ |
| $CONH_2$ | $OCH_3$ | $iC_3H_7$ |
| Cl | $CF_3$ | $iC_3H_7$ |
| CN | Br | $iC_3H_7$ |
| I | $CONH_2$ | $iC_3H_7$ |
| F | $COOCH_3$ | $iC_3H_7$ |
| Cl | Cl | $iC_3H_7$ |
| $OC_2H_5$ | $OCH_3$ | $iC_3H_7$ |
| $CF_3$ | CN | $iC_3H_7$ |
| $CONH_2$ | $CF_3$ | $iC_3H_7$ |
| $CF_3$ | $COOC_3H_7$ | $iC_3H_7$ |
| CN | CN | $C_6H_5$ |
| $CONH_2$ | CN | $C_6H_5$ |
| CN | $COOC_2H_5$ | $C_6H_5$ |
| $CONH_2$ | $COOCH_3$ | $C_6H_5$ |
| $COOC_3H_7$ | $COOCH_3$ | $C_6H_5$ |
| F | H | $C_6H_5$ |
| Cl | H | $C_6H_5$ |
| $CH_3$ | H | $C_6H_5$ |
| $C_2H_5$ | H | $C_6H_5$ |
| CN | H | $C_6H_5$ |
| $OCH_3$ | H | $C_6H_5$ |
| $OC_2H_5$ | H | $CH_3$ |
| $COOCH_3$ | H | $C_2H_5$ |
| F | Me | $C_3H_7$ |
| Cl | Me | $iC_3H_7$ |
| $C_2H_5$ | Me | $CH_3$ |
| CN | Me | $C_2H_5$ |
| $OCH_3$ | Me | $C_3H_7$ |
| $OC_2H_5$ | Me | $iC_3H_7$ |
| $COOC_2H_5$ | Me | $CH_3$ |
| F | CN | $C_2H_5$ |
| Cl | CN | $C_3H_7$ |
| $CH_3$ | CN | $iC_3H_7$ |
| $C_2H_5$ | CN | $CH_3$ |
| CN | CN | $C_2H_5$ |
| $OCH_3$ | CN | $C_3H_7$ |
| $OC_2H_5$ | CN | $iC_3H_7$ |

TABLE II-continued

| Starting Materials | | Product |
|---|---|---|

| $COOC_2H_5$ | CN | $CH_3$ |
|---|---|---|
| F | $COOCH_3$ | $C_2H_5$ |
| Cl | $COOC_2H_5$ | $C_3H_7$ |
| $CH_3$ | $COOC_3H_7$ | $iC_3H_7$ |
| $C_2H_5$ | $COOCH_3$ | $CH_3$ |
| CN | $COOC_2H_5$ | $C_2H_5$ |
| $OCH_3$ | $COOC_3H_7$ | $C_3H_7$ |
| $OC_2H_5$ | $COOCH_3$ | $iC_3H_7$ |
| $COOC_3H_7$ | $COOC_2H_5$ | $CH_3$ |

TABLE III

The above illustrative examples can be prepared where Z in the oxaloacetate sodium salt is methyl, ethyl, propyl, isopropyl, and phenyl, as well as where Z is hydrogen.

TABLE IV

The illustrative examples of Tables II and III can be converted to compounds where R is selected from the group consisting of hydrogen, an alkali metal or an amine cation, the amine selected from the group consisting of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2, 2',2"-nitrilotriethanol by standard methods.

For the sake of brevity, Tables III and IV are not rendered in the same manner as Table II but the same illustrative scoping is intended.

The following compounds are prepared in accordance with our invention. These compounds are not meant to limit but merely to exemplify the invention.

EXAMPLE 1

Dimethyl 1,4,6,9-tetrahydro-10-methyl-4,6-dioxopyrido[3,2-g]quinoline-2,8-dicarboxylate 30.0 g. of dimethylacetylene dicarboxylate is added dropwise to a solution of 12.2 g. of 2,6-diaminotoluene in 200 ml. methanol at room temperature. The reaction mixture is stirred at room temperature for 1 hour during which time the yellow product, a 1:2 adduct, precipitates and 24.8 g. is collected by filtration. An additional 10 g. of the product is obtained by stirring the filtrate for 24 hours. 5.0 g. of the 1:2 adduct is added to ca 250° refluxing Dowtherm A and the mixture is heated at the reflux temperature. Upon cooling, the yellow crystalline product precipitates and 3.3 are recovered. The compound is recrystallized from methanol-chloroform. The melting point is 291.5°–292.5° dec.

Anal. Calcd. for: $C_{17}H_{14}O_6N_2$: C, 59.65; H, 4.12; N, 8.18. Found: C, 58.83; H, 4.13; N, 7.94.

UV (ethanol) $\lambda$max 219 ($\epsilon$ 20,050), 227 sh (17,800), 257 (62,550), 276 sh (18,400) 290 sh (10,450), 315 sh (3,600), 357 (7,700), 375 (13,650) and 405 (9,450).

IR (nujol) 3400, 1734, 1640, 1610, 1590, 1510, 1265, 1160, 1020, 1010, 930, 865, 785.

EXAMPLE 2

Diethyl 1,4,6,9-tetrahydro-10-methyl-4,6-dioxopyrido[3,2-g]quinoline-2,8-dicarboxylate A mixture of 12.2 g. 2,6-diaminotoluene, 42 g. of the sodium salt of diethyloxaloacetate, and 100 ml. of glacial acetic acid is heated at 50° C. for 4 hours and is then allowed to stand at room temperature for 18 hours. The mixture is poured into ice water and made basic to pH 8 with 35% aqueous sodium hydroxide. The resulting solution is extracted with ether three times with a 200 ml. portion and four times with 200 ml. of 0.5 N sodium hydroxide. It is then dried with anhydrous sodium sulfate and the solvent removed. A brown oil solidifies upon standing. Recrystallization from Skellysolve B gives the diethyl diadduct as yellow needles. This adduct is added to boiling Dowtherm A and the compound isolated.

EXAMPLE 3

Disodium 1,4,6,9-tetrahydro-10-methyl 4,6-dioxopyrido[3,2-g]quinoline-2-8-dicarboxylate Either of the products of Example 1 or 2 is treated with 5% aqueous sodium hydroxide at reflux for 1.5 hours and the solution cooled. The sodium salt is recovered.

EXAMPLE 4

1,4,6,9-tetrahydro-10-methyl-4,6-dioxopyrido[3,2-g]quinoline-2,8-dicarboxylic acid The cooled solution of Example 3 is acidified with concentrated HCl and the dicarboxy acid precipitates as a bright yellow crystalline solid. The product is collected by filtration, washed with water and dried at reduced pressure at 60° C. It has a melting point greater than 310° C.

EXAMPLE 5

Di(tris-hydroxymethyl)methylammonium 1,4,6,9-tetrahydro-10-methyl-4,6-dioxopyrido-[3,2-g]quinoline-2,8-dicarboxylate 1.0 g. of the dicarboxylic acid prepared in Example 4 is added to 10 ml. of water. 0.77 g. of tris(hydroxymethyl)aminomethane is added. The mixture is heated for several minutes until solution is complete. The crystalline amine salt is precipitated with the addition of methanol.

EXAMPLE 6

Dimethyl-10-chloro-1,4,6,9-tetrahydro-4,6-dioxopyrido[3,2-g]quinoline-2,8-dicarboxylate A solution of 1 ml. of concentrated hydrochloric acid in 5 ml. of 5% ethanol is slowly added to a refluxing mixture of 10.1 g. of 1-chloro-2,6-dinitrobenzene, electrolytically reduced iron and 20 ml. of 50% ethanol. The mixture is heated at reflux for 2 hours. The mixture is allowed to cool slightly and the pH is adjusted to 8 with sodium hydroxide solution. The iron products are removed by filtration. The solvent is removed from the filtrate to leave a solid which is dissolved in water and extracted with methylene chloride. Removal of the solvents leaves an oily solid which upon recrystallization of from Skellysolve B gives off-white crystals of 2-chloro-1,3-diaminobenzene having a melting point of 82°–83.5° C.

11.0 g. of dimethylacetylene dicarboxylate is added dropwise to a solution of 5.25 g. of 2-chloro-1,3-diaminobenzene in 100 ml. of methanol at room temperature. The mixture is stirred for 2 hours at room temperature and the resulting yellow solid is collected by filtration. The solid is washed with 20 to 50 ml. of methanol, dried under vacuum at 60° C., and recrystallized from acetone. The tetramethyl[2-chloro-m-phenylene-diamino]dimaleate melts at 202.5°–204.5°C.

Anal. Calcd. for: $C_{18}H_{19}O_8N_2Cl$: C, 50.54; H, 4.49; N, 6.56; Cl, 8.31. Found: C, 50.38; H, 4.44; N, 6.86; Cl, 8.45.

UV (ethanol) max 226 ($\epsilon$ 19,200), 327 (28,000).

IR (nujol) NH 3270, C—O 1735, 1670.

9.35 g. tetramethyl[2-chloro-m-phenylene)-diamino]dimaleate is added to 125 ml. of Dowtherm A refluxing at about 255° C. over a period of 5 minutes. The mixture is refluxed for an additional 5 minutes and then cooled to room temperature. The resulting yellow solid is filtered, washed with acetone and dried. Recrystallization from a 1:1 mixture of methylene dichloride and methanol gives yellow needles having a melting point of 266°–267° C.

Anal. Calcd. for: $C_{10}H_{11}O_6N_2Cl$: C, 53.07; H, 3.06; N, 7.74; Cl, 9.79. Found: C, 53.04; H, 3.07; N, 7.83; Cl, 9.86.

UV (ethanol) $\lambda$ max 214 ($\epsilon$18,750), 230 sh (18,800), 243 (51,950), 290 sh (12,000), 295 sh (9,700), 210 sh (3,550), 360 sh (8,660), 379 (14,650), 400 sh (8,600).

IR (Nujol) 3360, 1745.

Mass spec. 362 mol. ion.

EXAMPLE 7

10-chloro-1,4,6,9-tetrahydro-4,6-dioxopyrido[3,2-g]quinoline-2,8-dicarboxylic acid 1.05 g. of the diester compound prepared in Example 6 is heated at reflux for 1 hour in 20 ml. of 5% sodium hydroxide. The mixture is cooled, 10 ml. of water added, and the pH adjusted to 3 with concentrated hydrochloric acid. The bright yellow diacid is collected by filtration. It has a melting point greater than 310° C.

EXAMPLE 8

Disodium 10-chloro-1,4,6,9-tetrahydro-4,6-dioxopyrido[3,2-g]quinoline-2,8-dicarboxylate The diacid prepared in Example 7 is dissolved in hot 4% sodium bicarbonate. Upon cooling, the disodium salt precipitates and is collected by filtration. Recrystallization from water gives a yellow solid melting above 310° C.

Anal. Calcd. for: $C_{14}H_5O_6N_2ClNa_2$: C, 44.41; H, 1.33; N, 7.40; Cl, 9.36. Found: C, 44.05; H, 1.30; N, 7.24; Cl, 9.33.

UR ($H_2O$) $\lambda$ max 214 ($\epsilon$21,150), 259 (65,800), 296 sh (4,750), 305 sh (3,000), 350 sh (5,750), 367 (9,500), 395.5 (9,950), 409 (10,950);

IR (nujol) 3310, 1705, 1675, 1650, 1630, 1600, 1575, 1505.

EXAMPLE 9

Di(tris-hydroxymethyl)methylammonium 10-chloro-1,4,6,9-tetrahydro-4,6-dioxopyrido[3,2-g]quinoline-dicarboxylate A solution of 4.0 g. disodium 10-chloro-1,4,6,9-tetrahydro-4,6-dioxopyrido[3,2-g]quinoline-2,8-dicarboxylate dissolved in 100 ml. of water is acidified with concentrated HCl to give the desired diacid as a yellow crystalline solid. The product is collected by filtration and dried. The diacid is converted to the disalt by adding 4.0 g tris(hydroxymethyl)aminomethane and dissolving the mixture in 15 ml. of water to which 200 ml. of methanol is added. The mixture is allowed to stand 18 hours at room temperature. The yellow crystalline product is collected by filtration, washed well with methanol and dried. It has a melting point greater than 310° C., with sintering at 250°.

Anal.

UV ($H_2O$) 214 mu ($\epsilon$ 23,250), 259 ($\epsilon$ 71,200), 284 sh($\epsilon$ 11,150), 409 ($\epsilon$ 12,150).

IR (nujol) $\lambda$ max 3320, 3300–3100 (broad); 1625 (broad); 1570 sh. 1490, 1340, 1255, 1060, 805, 790.

EXAMPLE 10

Di(tris-hydroxymethyl)methylammoniumpyrido[3,2-g]quinoline-2,8-dicarboxylate

To a solution of 5 gm. of di(tris-hydroxymethyl)methylammonium 10-chloro-1,4,6,9-tetrahydro-4,6-dioxopyrido[4,3-g]quinoline-2,8-dicarboxylate in 100 ml. of water is added 2.0 g. of 5% palladium-on-charcoal catalyst and 5.0 g. of magnesium oxide. The resulting mixture is hydrogenated at an initial pressure of 3 atmospheres of hydrogen until 1 mole of hydrogen has been absorbed. The mixture is filtered and the filtrate acidified by the addition of dilute hydrochloric acid. The resulting precipitate is removed by filtration. The 1,4,6,9-tetrahydro-4,6-dioxopyrido[3,2-g]quinoline-2,8-dicarboxylic acid obtained is converted to di(tris-hydroxymethyl)methylammonium 1,4,6,9-tetrahydro-4,6-dioxopyrido[3,2-g]quinoline-2,8-dicarboxylate by adding two equivalents of (tris-hydroxymethyl)methylamine in aqueous solution. The crystalline product is recovered after addition of methanol.

EXAMPLE 11

10-Chloro-1,4,6,9-tetrahydro-4,6-dioxo-5-(trifluoromethyl)pyrido[3,2-g]quinoline-2,8-dicarboxylic acid a. 2-Chloro-5-$\alpha,\alpha,\alpha$-trifluoromethyl-m-phenylenediamine To a stirred solution of 90.24 grams (0.4 mole) of stannous chloride dihydrate in 220 ml. of concentrated HCl is added, portionwise, 15.22 grams (0.0564 mole) of 3.5-dinitro-4-chlorobenzotrifluoride obtained from Pierce Chem. Co. The mixture is warned to 60°, stirred, and allowed to cool to room temperature and then stirred at room temperature for 5 hours and allowed to stand over night.

To the mixture is added slowly, with cooling, a 50% solution of sodium hydroxide until the mixture is strongly basic. The insoluble material is removed by filtration, dissolved in water and washed well with methylene chloride. The filtrate is extracted with additional $CH_2Cl_2$. The methylene chloride extracts are dried over anhydrous $MgSO_4$ and the solvent removed. The combined solid is recrystallized from ethanol-water. There is obtained 9.02 grams melting at 95.6°.

b. Dimethyl 10-chloro-1,4,6,9-tetrahydro-4,6-dioxo-5-(trifluoromethyl)pyrido[3,2-g]-quinoline-2,8-dicarboxylate To a solution of 8.52 grams (0.0404 mole) of 2-chloro-5-$\alpha,\alpha,\alpha$-trifluoromethyl-m-phenylenediamine in 140 ml. of methanol is added dropwise, with stirring, 11.93 grams (0.084 mole) of dimethyl acetylene dicarboxylate. Stirring is continued for 5 hours. The yellow precipitate is removed by filtration. There is obtained 6.40 grams of material melting at 205–8°. Evaporation of the filtrate gives an additional 6.10 grams of material melting at 203–6°.

To a refluxing mixture of 100 ml. of Dowtherm A is added 9.88 grams of the material obtained above. Refluxing is continued for 30 minutes. The mixture is cooled to room temperature, the precipitate removed by filtration and washed with Skellysolve B and then boiled with ethanol. The mixture is allowed to cool and the solid removed by filtration. There is obtained 2.29 grams of material melting at 273° (dec.).

Analysis for: $C_{17}H_{10}ClF_3N_2O_6$: Calcd.: C, 47.40; H, 2.34; Cl, 8.23; F, 13.23; Found: 6.51%. Found: C, 48.02; H, 2.40; Cl, 7.71; F, 13.43; N, 6,66%.

The IR spectra is in agreement.

c. Product

A mixture of 1.65 grams (0.0058 mole) of dimethyl 10-chloro-1,4,6,9-tetrahydro-4,6-dioxo-5-(trifluoromethyl)pyrido[3,2-g]quinoline-2,8-dicarboxylate and 20 ml. of water is stirred and to the mixture is added a 5% sodium hydroxide solution until solution occurs (3ml.). The solution is stirred for 15 minutes and then acidified by the addition of a dilute HCl solution. The resulting tan precipitate is removed by filtration and washed with water. There is obtained 1.11 gram of material melting above 300°.

Anal. Calcd. for $C_{15}H_6ClF_3N_2O_6$: F, 14.16%. Found: F, 13.95%.

EXAMPLE 12

1,4,6,9-Tetrahydro-4,6-dioxopyrido[3,2-g]-quinoline-2,8,10-tricarboxylic acid a. Methyl 2,6-dinitrobenzoate 2,6-Dinitrobenzoic acid (10.6 grams) is suspended in ether (125 ml.) at 0°C. 1-Methyl-3-p-tolyltriazine (8.2 grams) in ether (75 ml.) is added dropwise to the stirred reaction mixture in an ice bath. The reaction mixture is stirred at 0° for 1 hour and at room temperature for 1 hour. The reaction mixture is diluted to 1 l. with ether and the insoluble product collected by filtration. Recrystallization from methanol gives colorless crystals (3.65 grams, melting point 150°–151.5°). An additional 4.1 grams of product are obtained from the filtrate.

Analysis; Calcd.: C, 42.49; H, 2.67; N, 12.39. Found: C, 42.55; H, 2.74; N, 12.10.

ir (nujol): CH 3090; C=O, 1735: $NO_2$, 1350.

uv (EtOH): $\lambda_{max}$ ($\epsilon$) 233 (15,900), 295 sh (984).

b. Tetramethyl 2,2'-(2-carbomethyloxyphenylene-1,3-diimino)dibutenedioate

Methyl 2,6-dinitrobenzoate (7.75 grams) is dissolved in methanol (250 ml.) and treated with 10% palladium on charcoal (0.8 gram) and hydrogen (40 psi) on a Parr Hydrogenator for 2 hours. The catalyst is removed by filtration and dimethyl acetylenedicarboxylate (15.0 grams) added slowly. The reaction mixture is allowed to stir at room temperature for 18 hours. The 1:2 adduct is collected by filtration (11.7 grams, melting point 147°–149°).

Analysis: Calcd.: C, 53.33; H, 4.92; N, 6.22. Found: C, 53.28; H, 4.93; N, 6.09.

ir (Nujol): NH, 3290, 3210; C=O 1735, 1724, 1685; C=C/C=N, 1605, 1580; aromatic CH 805.

uv (EtOH): $\lambda_{max}$ ($\epsilon$) 205 (17,400), 232 (18,800), 311 (21,900), 352 (24,200).

c. Trimethyl 1,4,6,9-tetrahydro-4,6-dioxopyrido[3,2-g]quinoline-2,8-10-tricarboxylate The 1:2 adduct (10.0 grams) is added to refluxing Dowtherm A. The reaction mixture is refluxed for seven minutes and then allowed to cool to room temperature. The yellow triester is collected by filtration, and washed with acetone and twice with hot chloroform. The insoluble solid is homogeneous by thin layer chromatography (2.67 grams, melting point 282°–286°dec.).

Analysis:
ir (Nujol): NH/OH 3320, 3200, 3080; C=O 1760, 1725, 1695; aromatic CH 805, 780.
uv (MeOH): $\lambda_{max}$ ($\epsilon$) 210 (26,800), 226 sh (20,000), 257 (52,900), 397 sh (19,700), 409 (21,300), d. Product The triester (1.0 gram) is dissolved in 1.0 N sodium hydroxide (15 ml.). After stirring for a few minutes, the sodium salt precipitates. This solid is collected and dissolved in water and the pH adjusted to pH=3 with 3M hydrochloric acid. The solid diacid is collected by filtration, washed with water. and dried in a vacuum oven (1.0 gram, melting point > 320°).

Analysis:
ir (Nujol): OH/NH 3480, 3270; =CH 3080, C=O 1725.
uv (H$_2$O): $\lambda_{max}$ ($\epsilon$) 214 (22,100), 219 sh (21,350), 264 (48,500), 286 sh (7,550), 298 sh (2,300), 387 (12,700), 408 (10,500), 427 (11,350).

EXAMPLE 13

10-Chloro-1,4,6,9-tetrahydro-5-methyl-4,6-dioxopyrido[3,2-g]quinoline-2,8-dicarboxylic acid a. 4-Chloro-3,5-toluenediamine 3,5-Dinitro-4-chlorotoluene (100 grams) is dissolved in ethanol (165 ml.) and 125 ml. of water is added slowly to the refluxing mixture. Ethanol is added from time to time to insure complete solution. Electrolytically reduced iron powder (167 grams) is added to the reaction mixture. A solution of concentrated hydrochloric acid (10 ml.) in 1:1 ethanol-water (50 ml.) is added carefully. The reaction mixture is refluxed for 2 hours, cooled slightly, and the pH adjusted to pH=8 with 20% sodium hydroxide. The inorganic precipitate is removed by filtration and the filtrate evaporated to leave dark solid. The solid is partially dissolved in benzene and the remaining inorganic matter removed. The filtrate is evaporated to dryness and the desired diamine is isolated by extraction from the residue with Skellysolve B. Recrystallization from Skellysolve B gives tan plates (54.2 grams, melting point 115°–116°).

Analysis for: C$_7$H$_9$N$_2$Cl: Calcd.: C, 53.71; H, 5.97; N, 17.90; Cl, 22.66.

Found: C, 53.82; H, 5.76; N, 18.27; Cl, 22.70.

ir (Nujol): NH 3410, 3350, 3300, 3180; NH/C=C 1610, 1595 sh, 1490; aromatic CH/C—Cl 840, 825, 815.

uv (EtOH): $\lambda_{max}$ ($\epsilon$) 217 (38,500), 246 sh (7,250) 293 (1,900).

b. Tetramethyl 2,2'-(2-chlorotoluene-3,5-diimino)-dibutenedioate

4-Chloro-3,5-toluenediamine (35 grams) is dissolved in methanol (500 ml.) and dimethyl acetylenedicarboxylate (75 grams) is added slowly. The reaction mixture is stirred for 18 hours and the resulting solid 1:2 adduct is collected by filtration (54.35 grams, melting point 209–11°), Recrystallization from acetone gives a crystalline solid (mp. 216.5°–218°).

Analysis for: C$_{19}$H$_{21}$O$_8$N$_2$Cl: Calcd.: C, 51.76; H, 4.80; N, 6.36; Cl, 8.04. Found: C, 51.71; H, 4.81; N, 6.07; Cl, 8.00.

ir (Nujol): NH 3250, C=O 1740, 1670, C=O/NH def on C=N 1615, 1535, 1515.

uv (EtOH): 227 (21,650;, 327 (28,250).

c. Dimethyl 10-chloro-1,4,6,9-tetrahydro-5-methyl-4,6-dioxopyrido[3,2-g]quinoline-2,8-dicarboxylate The 1:2 adduct (66.2 grams) is added to refluxing Dowtherm A and the reaction mixture is refluxed for 15 minutes. The reaction mixture is allowed to cool to room temperature and the resulting solid collected by filtration (50.8 grams, melting point 275°–280° dec.). Multiple recrystallization from chloroform gives a yellow crystalline product (38.8 grams, melting point 278–80°dec.).

Analysis for: C$_{17}$H$_{13}$O$_6$N$_2$Cl: Calcd.: C, 54.19; H, 3.48; N, 7.44; Cl, 9.41. Found: C, 53.94; H, 3.50; N, 7.26; Cl, 12.61.

uv (EtOH): $\lambda_{max}$ ($\epsilon$) 400 sh (7,300), 370 (12,050), 287 sh (18,300), 277 sh (20,450), 254 (43,650), 235 sh (18,550), 215 sh (16,950), 209 (17,650).

ir (Nujol): NH 3360, 3350; =CH 3060; C=O 1730, 1720.

d. Product

The diester (38.8 grams) is stirred in 1.0 N NaOH (350 ml.) The initial solid dissolves but a new solid precipitates within a few minutes. The reaction mixture is diluted to 1.5 l. with water and the pH adjusted to pH=4 with 3 N hydrochloric acid. The yellow diacid is collected by filtration, washed several times with water and then with acetone, and dried in a vacuum oven (38.2 grams).

EXAMPLE 14

1,4,6,9-Tetrahydro-10-methoxy-4,6-dioxopyrido[3,2-g]quinoline-2,8-dicarboxylic acid a. 2,6-Dinitroanisole Chlorodinitrobenzene (20.0 grams) is dissolved in anhydrous methanol (100 ml.). Sodium methoxide solution (25% in methanol, 14 ml.) is added and the mixture stirred at room temperature for 18 hours. The reaction mixture is poured into water (500 ml.) and the resulting solution extracted with ether (3 × 200 ml.). The combined ether extracts are washed with water (100 ml.), and dried with anhydrous sodium sulfate. Removal of the solvent leaves a solid which gives yellow needles after Darco treatment and recrystallization from ethanol (11.15 gram, melting point 118°).

Analysis for: C$_7$H$_6$N$_2$O$_5$: Calcd.: C, 42.43; H, 3.05; N, 14.14. Found: C, 42.39; H, 3.08; N, 14.13.

iv (Nujol): C=C/NO$_2$ 1610, 1580, 1525; C—O 1265, 980.

uv (EtOH): $\lambda_{max}$ ($\epsilon$) 227 sh (10,300), 300 (1950).

b. Tetramethyl 2,2'H(2-methoxyphenylene-1,3-diimino)dibutenedioate 2,6-Dinitroanisole (10.0 grams) is dissolved in methanol (150 ml.) and 5% palladium on charcoal (1.0 gram) added. The mixture is treated with hydrogen at 40 psi on the Parr Hydrogenator until the uptake of hydrogen stops. The catalyst is removed by filtration and dimethyl acetylenedicarboxylate (16.0 grams) added slowly to the filtrate. The reaction mixture is stirred for 18 hours. The resulting solid (10.3 grams) is collected by filtration. Additional crops (7.9 grams) are obtained from the concentrated filtrate. Recrystallization from methanol gives yellow crystals (18.0 grams) melting point 105°–110°).

Analysis for: $C_{19}H_{22}O_9N_2$: Calcd.: C, 54.02; H, 5.25; N, 6.63. Found: C, 53.84; H, 5.17; N, 6.13.

ir (Nujol): NH 3240; C=O 1740; aromatic CH 790, 780.

iv (EtOH): $\lambda_{max}$ ($\epsilon$) 224 (20,000), 332 (29,450).

c. Dimethyl 1,4,6,9-tetrahydro- 10-methoxy-4,6-dioxopyrido[3-2-g]quinoline-2,8-cicarboxylate The 1:2 adduct (12 grams) is added carefully to refluxing Dowtherm A (100 ml.). The mixture is heated at reflux for three minutes and then allowed to cool to room temperature. The solid precipitate (7.94 grams) is collected and washed with acetone. Recrystallization from methanol-chloroform gives yellow crystals (melting point 291° dec.).

Analysis for: $C_{23}H_{30}O_8N_2$: Calcd.: C, 56.98; N, 3.94; N, 7.82. Found: C, 57.02; N, 4.08; N, 7.88.

ir (Nujol): NH/OH 3390, 3330, 3250, 1735 C=O or C=N/C=C 1640, 1585, 1520.

uv (EtOH): $\lambda_{max}$ ($\epsilon$) 218 (18,100), 234, sh (16,800), 257 (50,650), 288 sh (14,000), 357 (7,600), 373 : 11,100), 407 (12,850), 445 sh (2,250).

d. Product

The diester (1.0 gram) is stirred in 1.0 N sodium hydroxide (150 ml.) for 10 minutes. The pH of the resulting solution is adjusted to pH=3 with concentrated hydrochloric acid. The yellow diacid is collected by filtration and washed with water (0.69 gram, melting point 305°dec.).

EXAMPLE 15

10-Fluoro-1,4,6,9-tetrahydro-4,6-dioxopyrido[3,2-g]quinoline-2,8-dicarboxylic acid a. 1-Fluoro-2,6-dinitrobenzene A mixture of 1-chloro-2,6-dinitrobenzene (30 grams), anhydrous potassium fluoride (35 grams), and dimethylformamide (50 ml.) is refluxed for 24 hours. The reaction mixture is poured into water (250 ml.) and extracted with ether (3 × 100 ml.). The combined ether extracts are dried with anhydrous sodium sulfate. Removal of the solvent leaves brown solid. Chromatography of the solid on silica gel with methylene chloride as the elutant gives a light yellow solid after recrystallization from pentane-methylene chloride. (20.30 grams, melting point 50°).

Mass spectrum (70 ev) mol. ion 186 m/e.

b. Tetramethyl 2,2′(2-fluorophenylenediimino)dibutenedioate

1-Fluoro-2,6-dinitrobenzene (15 grams) in methanol (300 ml.) is treated with 10% palladium on charcoal (1.5 gram) and hydrogen (40 psi) on a Parr Hydrogenator until hydrogen uptake ceases. The solvent is removed on a small aliquot to leave a colorless oil. Since this oil does not cyrstallize easily, the remaining solution is used directly. Dimethyl acetylenedicarboxylate (25 grams) is added to the hydrogenated solution and the resulting mixture stirred for 4 hours. The yellow 1:2 adduct is collected by filtration (18.8 grams, melting point 170°–174°). Recrystallization from methanol gives yellow crystals.

Analysis for: $C_{18}H_{19}O_8N_2F$: Calcd.: C, 52.68; H, 4.67; N, 6.83; F, 4.63. Found: C, 52.53; H, 4.72; N, 6.99; F, 3.27.

ir (Nujol): NH 3290; C=O 1735, 1670; C—O/C—F/-C—N/1275, 1220, 1190, 1140, 1030.

uv (EtOH): $\lambda_{max}$ ($\epsilon$) 219 (18,400), 245 sh (10,950), 327 (29,800).

c. Dimethyl 10-fluoro-1,4,6,9-tetrahydro-4,6-dioxopyrido[3,2-g]quinoline-2,8-dicarboxylate The 1:2 adduct (15 grams) is added to refluxing Dowtherm A and refluxed for four minutes. A yellowish solid precipitates from the reaction mixture as it cools. This solid is collected by filtration (7.05 grams, melting point 310°–319° dec.)

d. Product

The diester (1.0 gram) is stirred in 1.0 N sodium hydroxide (35 ml.) for 1 hour. The reaction mixture is added to 50 ml. of water and the pH of the resulting solution adjusted to pH=3 with concentrated hydrochloric acid. The diacid is collected by filtration, washed with acetone, and dried in a vacuum oven (0.95 gram).

EXAMPLE 16

1,4,6,9-Tetrahydro-3,7-10-trimethyl-4,6-dioxopyrido[3,2-g]quinoline-2,8-dicarboxylic acid a. Tetramethyl 2,2′-dimethyl-3,3′-(2-methylphenylene)dibutenedioate A mixture of 2,6-diaminotoluene (10 grams), benzene (250 ml.), diethyl oxalpropionate and 0.5 gram p-toluenesulfonic acid is refluxed for 18 hours with constant water removal. A small amount yellow solid (0.5 gram) precipitates from the cooled reaction mixture to leave a reddish oil which crystallizes when trituated with methanol (12.2 grams). The 1:2 adduct is recrystallized from methanol to give yellow crystals (melting point 90°).

Analysis for: $C_{25}H_{34}O_8N_2$: Calcd.: C, 61.22; H, 6.94; N, 5.71. Found: C, 60.79; H, 7.00; N, 5.66.

ir (Nujol): NH 3220, 3170; C=O 1725; aromatic CH 770.

uv (EtOH): $\lambda_{max}$ ($\epsilon$) 228 (11,150), 246 sh (9,500), 328 (28,850).

b. Diethyl 1,4,6,9-tetrahydro-3,7-10-trimethyl-4,6-dioxopyrido[3,2-g]quinoline-2,8-dicarboxylate The 1:2 adduct (10 grams) is added to refluxing Dowtherm A (125 ml.) and refluxed for 5 minutes. The mixture is allowed to cool to room temperature and the resulting diester collected by filtration (8.1 grams, melting point 248°–255°).

Analysis:

ir (Nujol): NH/OH 3490, 3430, 3380, 3250, 3170; NH/=CH 3090; C=O 1740, 1700.

uv (EtOH): $\lambda_{max}$ ($\epsilon$) 208 (16,200), 218 (16,650), 263 (64,250), 293 sh (11,400), 383 (11,000), 405 sh (9,100).

c. Product

The diester (6.0 grams) is stirred in 1.0 N NaOH (100 ml.) until the solid dissolves (ca. 0.5 hr). The reaction mixture is poured into water (100 ml.) and the pH adjusted to pH=3 with concentrated hydrochloric acid. The diacid is collected as a yellow solid, washed sequentially with water and acetone, and dried in a vacuum oven (5.29 grams).

EXAMPLE 17

10-Cyano-1,4,6,9-tetrahydro-4,6-dioxopyrido(3,2-g)quinoline-2,8-dicarboxylic acid a. 2,6-Dinitrobenzonitrile 1-Chloro-2,6-dinitrobenzene (40.4 grams) is dissolved in anhydrous dimethylformamide (200 ml.). Cuprous cyanide (72 grams) is added and the stirred reaction mixture is heated to reflux for 6 hours. The dark brown reaction mixture is cooled and poured into water (1.5 l.) with stirring. The tan precipitate is collected by filtration and then extracted three times with hot ethanol (300 ml.). Removal of two-thirds of the solvent from combined ethanol extracts under reduced pressure gives a tan precipitate. The precipitate is collected by filtration and recrystallized from ethanol to give a tan product (7.2 grams) melting at 143°–146.5°.

b. 2,6-Diaminobenzonitrile 2,6-Dinitrobenzonitrile (10.0 grams) is added in portions to a stirred solution of stannous chloride (82.5 grams) is concentrated HCl (230 ml.) at room temperature. Stirring is continued at room temperature for ½ hours, then the reaction mixture is cooled to 0° and made strongly basic with 50% NaOH. The reaction mixture is diluted with water (1 l.) and extracted four times with methylenechloride (200 ml.). The combined extracts are washed once with water (200 ml.), dried over sodium sulfate, then taken to dryness under reduced pressure. Recrystallization of the crude solid (4.6 grams) from benzene-Skellysolve B gives the product (4.15 grams) melting at 91°–92°.

c. Tetramethyl 2,2'-(2-cyano-phenylene-1,3-diimino)-dibutenedioate

Dimethylacetylene dicarboxylate (9.5 grams) is added dropwise to a stirred solution of 2,6-diaminobenzonitrile (4.0 grams) in methanol (50 ml.) at room temperature. The reaction mixture is stirred at room temperature for 18 hours, during which time the yellow product, a 1:2 adduct, precipitates and is collected by filtration (5.15 grams), melting point 160°–210°. Recrystallization from acetone gives a material (2.43 grams) melting at 218°–220° (dec.). Additional crops totaling 7.5 grams are obtained from the methonal filtrate when stirred for 72 hours at room temperature.

d. Dimethyl 10-cyano-1,4,6,9-tetrahydro-4,6-dioxopyrido[3,2-g]quinoline-2,8-dicarboxylate The 1:2 adduct (1.0 gram) is added to refluxing Dowtherm A (ca. 250°) and the mixture heated at reflux for 10 minutes. Upon cooling, the tan crystalline product precipitates (0.70 gram), melting point 282° (dec.). Chromatography on silica gel gives the pure yellow product (0.42 gram) melting point 281°–283° (dec.).

Analysis for: $C_{17}H_{11}O_6N_3$: Calcd.: C, 57.79; H, 3.14; N, 11.90. Found: C, 58.13; H, 3.23; N, 12.11.

e. Product

The dimethyl ester (0.40 gram) is dissolved in 1M NaOH (15 ml.) and stirred at room temperature for one-half hour. The solution is acidified with 3M HCl to give the desired diacid as a yellow crystalline solid. The product is collected by filtration, washed with water and dried at reduced pressure at 60° (0.35 gram), melting point >320°. Recrystallization of 50 mg. from water gives a material with a melting point >320°.

Analysis for: $C_{15}H_7O_6N_3 \cdot \frac{1}{2}H_2O$: Calcd.: C, 53.90; H, 2.41; N, 12.57. Found: C, 54.24; H, 2.14; N, 12.65.

EXAMPLE 18

5-Methyl-1,4,6,9-tetrahydro-4,6-dioxopyrido[3,2-g]quinoline-2,8,-10-tricarboxylic acid a. Methyl 2,6-dinitrobenzoate 2,6-Dinitrotoluic acid (10. gram) is suspended in ether (125 ml.) at 0°C. 1-Methyl-3-p-tolyltriazene (8.2 grams) in ether (75 ml.) is added dropwise to the stirred reaction mixture in an ice bath. The reaction mixture is stirred at 0° for 1 hour and at room temperature for 1 hour. The reaction mixture is diluted to 1 l. with ether and the insoluble product collected by filtration. Recrystallization from methanol gives a crystalline solid.

b. Tetramethyl 2,2'-(2-carboxymethoxy-5-methylphenylene-1,3-diimino) dibutenedioate Methyl 2,6-dinitrotoluate (7.75 grams) is dissolved in methanol (250 ml.) and treated with 10% palladium on charcoal (0.8 gram) and hydrogen (40 psi) on a Parr Hydrogenator for 2 hours. The catalyst is removed by filtration and dimethyl acetylenedicarboxylate (15.0 grams) is added slowly. The reaction mixture is allowed to stir at room temperature for 18 hours. The 1:2 adduct is collected by filtration.

c. Trimethyl 1,4,6,9-tetrahydro-5-methyl-4,6-dioxopyrido[3,2-g]quinoline-2,8,-10-tricarboxylate The 1:2 adduct (10.0 grams) is added to refluxing Dowtherm A. The reaction mixture is refluxed for seven minutes and then allowed to cool to room temperature. The triester is collected by filtration and washed with acetone and twice with hot chloroform. The insoluble solid is homogeneous by thin layer chromatography.

d. Product

The triester (1.0 gram) is dissolved in 1.0 N sodium hydroxide (15 ml.). After stirring for a few minutes, the sodium salt precipitates. This solid is collected and dissolved in water and the pH is adjusted to pH=3 with 3M hydrochloric acid. The solid diacid is collected by filtration, washed with water and dried in a vacuum oven.

EXAMPLE 19

10-Cyano-1,4,6,9-tetrahydro-5-methyl-4,6-dioxopyrido[3,2-g]quinoline-2,8-dicarboxylic acid a. 2,6-Diamino-p-tolunitrile 2,6-Dinitro-p-tolunitrile (10 grams) is added in portions to a stirred solution of stannous chloride (82.5 grams) in concentrated HCl (230 ml.) at room temperature. Stirring is continued at room temperature for ½ hours. The reaction mixture is cooled to 0° and made strongly basic with 50% NaOH. The reaction mixture is diluted with water (1 l.) and extracted four times with methylene chloride (200 ml.). The combined extracts are washed once with water (200 ml.) dried over sodium sulfate and then taken to dryness under reduced pressure. Recrystallization of the crude solid from benzene-Skellysolve B gives 2,6-diaminotolunitrile.

b. Tetramethyl 2,2'-(2-cyano-5-methylphenylene-1,3-diimino) dibutenedioate

Dimethylacetylene dicarboxylate (9.5 grams) is added dropwise to a stirred solution of 2,6-diaminotolunitrile (4.0 grams) in methanol (50 ml.) at room temperature. The reaction mixture is stirred at room temperature for 48 hours during which time the product precipitates and is collected by filtration. Recrystallization from acetone gives the 1:2 adduct.

c. Dimethyl 10-cyano-1,4,6,9-tetrahydro-5-methyl-4,6-dioxopyrido[3,2-g]quinoline-2,8-dicarboxylate Tetramethyl 2,2'-(2-cyano-5-methylphenylene-1,3-diimino)-dibutenedioate (1.0 gram) is added to refluxing Dowtherm A (ca. 250°) and the mixture heated at reflux for 10 minutes. Upon cooling, the crystalline product precipitates. Chromatography on silica gel gives the pure product.

d. Product

The dimethyl ester (0.40 gram) is dissolved in 1M NaOH (15 ml.) and stirred at room temperature for one-half hour. The solution is acidified with 3M HCl to give the desired diacid as a crystalline solid. The product is collected by filtration, washed with water and dried at reduced pressure at 60°.

EXAMPLE 20

Tris(hydroxymethyl)aminomethane (THAM) salts of Examples 11–19

The tris(hydroxymethyl)aminomethane salts of the products of Examples 11–19 are prepared by dissolving the acid in aqueous tris(hydroxymethyl)aminomethane. Methanol is added to the solution and the precipitate is collected.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula Ia. The preferred method of administration is by inhalation into the lung by means of an aerosol liquid or powder for insufflation. A preferred dosing schedule for repeated administration of the compounds of this invention is disclosed in a later portion of this specification.

For oral administration either solid or fluid unit dosage forms can be prepared. For preparing solid compositions such as tablets, the compound of Formula Ia is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula Ia in water and adding salt to provide a isotonic solution and buffering to a pH compatible with inhalation. The solutions are dispersed in a spray device or nebulizer and sprayed into the mouth while inhaling.

Aerosols are prepared by dissolving a compound of the Formula Ia in water or ethanol and mixing with a volatile propellant and placing in a pressurized container having a metering valve to release a predetermined amount of material.

The liquefied propellant employed in one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration. A dosage schedule of from about 0.01 to about 50 mg. of compound in a single dose administered parenterally or by inhalation in the compositions of this invention is effective for preventing allergy attacks. More specifically, the single dose is from about 0.01 to about 10 mg. of compound. The oral and rectal dose is from about 0.1 to about 500 mg. in a single dose. More specifically, the single dose is from about 0.1 to about 50 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 1.0 mg. of the tris(hydroxymethyl)aminomethane salt of 10-chloro-1,4,6,9-tetrahydro-5-methyl-4,6-dioxopyrido[3,2-g]quinoline-2,8-dicarboxylic acid. Four hours later the individual insufflates 0.02 mg. of the same compound and every 4 to 6 hours thereafter insufflates 0.02 mg. of the same compound until effective asthma prophylaxis is not provided. The individual then insufflates 1.0 mg. mg. of the same compound, then reduces the insufflation dosage to 0.02 mg. 4 to 6 hours later. The dosage schedule continues in this manner.

The administration of the compositions of the present invention to humans and animals provides a method for the prophylactic treatment of allergy or all anaphylactic reactions of a reagin or a non-reagin mediated nature. That is to say these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions are bronchial asthma, allergic rhinitis, food allergy, hay fever, urticaria, auto-immune diseases, exercise induced asthma, stress induced asthma, and bird fancier's disease.

EXAMPLE 21

A lot of 10,000 tablets, each containing 0.1 mg. of dimethyl 10-chloro-1,4,6,9-tetrahydro-4,6-dioxopyrido[3,2-g]quinoline-2,8-dicarboxylate is prepared from the following types and amounts of ingredients:

| | |
|---|---|
| Dimethyl 10-chloro-1,4,6,9-tetrahydro-4,6-dioxopyrido-[3,2-g]quinoline-2,8-dicarboxylate | 1 Gm. |
| Dicalcium phosphate | 1,500 Gm. |
| Methylcellulose, U.S.P. (15 cps.) | 60 Gm. |
| Talc | 150 Gm. |
| Corn starch | 200 Gm. |
| Magnesium stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of 1 tablet every 4 hours.

EXAMPLE 22

One thousand two-piece hard gelatin capsules, each containing 100 mg. of dimethyl 10-chloro-1,4,6,9-tetrahydro-4,6-dioxopyrido[3,2-g]quinoline-2,8-dicarboxylate are prepared from the following types and amounts of ingredients:

| | |
|---|---|
| Dimethyl 10-chloro-1,4,6,9-tetrahydro-4,6-dioxopyrido-[3,2-g]quinoline-2,8-dicarboxylate, micronized | 100 Gm. |
| Talc | 100 Gm. |
| Magnesium stearate | 1 Gm. |

The ingredients are mixed well and filled into capsules of the proper size.

Capsules so prepared are useful in preventing attacks of bronchial asthma at a dose of one capsule every six hours.

EXAMPLE 23

One thousand tablets, each containing 500 mg. of dimethyl 10-chloro-1,4,6,9-tetrahydro-4,6-dioxopyrido[3-2-g]quinoline-2,8-dicarboxylate are made from the following types and amounts of ingredients:

| | |
|---|---|
| Dimethyl 10-chloro-1,4,6,9-tetrahydro-4,6-dioxopyrido-[3,2-g]quinoline-2,8-dicarboxylate | 500 Gm. |
| Microcrystalline cellulose NF | 120 Gm. |
| Starch | 16 Gm. |
| Magnesium stearate powder | 4 Gm. |

The ingredients are screened and blended together and pressed into 640 mg. tablets.

The tablets are useful to protect against food allergy at a dose of 1 tablet before meals.

EXAMPLE 24

A sterile preparation suitable for intramuscular injection and containing 1 mg. of dimethyl 10-chloro-1,4,6,9-tetrahydroxy-4,6-dioxopyrido[3,2-g]quinoline-2,8-dicarboxylate in each milliliter is prepared from the following ingredients:

| | |
|---|---|
| Dimethyl 10-chloro-1,4,6,9-tetrahydroxy-4,6-dioxopyrido-[3,2-g]quinoline-2,8-dicarboxylate | 1 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for propylactic treatment of allergic rhinitis.

EXAMPLE 25

Aqueous Solution 600 ml. of an aqueous solution containing 0.1 mg. of the tris(hydroxymethyl)aminomethane salt of 10-chloro-1,4,6,9-tetrahydro-4,6-dioxopyrido[3,2-g]quinoline-2,8-dicarboxylic acid per ml. is prepared as follows:

| | |
|---|---|
| Tris(hydroxymethyl)aminomethane salt 10-chloro-1,4,6,9-tetrahydro-4,6-dioxopyrido[3,2-g]quinoline-2,8-dicarboxylic acid | 60 mg. |
| Sodium chloride | 5,400 mg. |
| Water for injection q.s. | 600 ml. |

The THAM salt and sodium chloride are dissolved in sufficient water to make 600 ml. and sterile filtered.

The solution is placed in nebulizers designed to deliver 0.25 ml. of solution per spray.

The solution is sprayed into the lungs every four hours for prevention of asthmatic attacks.

EXAMPLE 26

Powder for Insufflation

A powder mixture consisting of 100 mg. of tris-(hydroxymethyl)aminomethane salt of 10-chloro-1,4,6,9-tetrahydro-4,6-dioxopyrido[3,2-g]quinoline-2,8-dicarboxylic acid and sufficient lactose to make 5 gm. of mixture is micropulverized and placed in an insufflator designed to deliver 50 mg. of powder per dose.

The powder is inhaled into the lungs for prevention of asthmatic attacks.

The powder is inhaled into a nostril of the nose every 4 to 6 hours for prevention of rhinitis.

EXAMPLE 27

Aerosol

Twelve grams of an aerosol composition is prepared from the following ingredients:

| | |
|---|---|
| Tris(hydroxymethyl)aminomethane salt of 10-chloro-1,4,6,9-tetrahydro-4,6-dioxopyrido[3,2-g]quinoline-2,8-dicarboxylic acid | 0.015 Gm. |
| Freon 12 | 1.450 Gm. |
| Freon 114 | 2.160 Gm. |

-continued

| | |
|---|---|
| Water | 7.775 Gm. |
| Sorbitan monoleate | 0.600 Gm. |

The THAM salt is dissolved in water, chilled to −30°C., and added to the chilled Freons. The 12 grams of composition is added to a 13 cc. plastic coated bottle and capped with a metering valve, which releases 80 mg. of composition in an aerosol. The aerosol is inhaled every 6 hours for prevention of asthmatic attacks.

EXAMPLE 28

In individuals who require continual treatment in the Examples 21 through 27, the dosage of the Example is given initially and each succeeding administration of the drug is at 1/50 of the initial dosage. This maintenance dosing is continued until effective allergy prophylaxis is not obtained. The initial dosage of Examples 21 through 27 is then started once more, followed by the maintenance dosages.

EXAMPLE 29

After allowing for the differing solubilities of the compounds and the activity of the particular compound as measured, for example, by the in vivo rat passive cutaneous anaphylaxis assay, a suitable quantity of each of the compounds of Tables II, III and IV and particularly the compounds of this invention in Examples 11–19 are substituted for the active compound in the compositions and uses of Examples 21 through 27. Results showing anti-allergy activity are obtained.

EXAMPLE 30

The rat passive cutaneous anaphylaxis assay is run in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots over the number of animals.

The tris(hydroxymethyl)aminomethane salt of the following compounds are prepared by dissolving the carboxylic acid in an equivalent weight of aqueous tris(hydroxymethyl)aminomethane and is tested in the rat passive cutaneous anaphylaxis assay in the above manner.

The inhibitory dose$_{50}$ for the tris(hydroxymethyl)aminomethane salts of compounds of the invention, when

| THAM salt of | Inhibitory Dose$_{50}$, mg./kg. |
|---|---|
| 1,4,6,9-Tetrahydro-10-methoxy-4,6-dioxopyrido[3,2-g]quinoline-2,8-dicarboxylic acid | 0.05 |

-continued

| THAM salt of | Inhibitory Dose₅₀ mg./kg. |
|---|---|
| 10-Cyano-1,4,6,9-tetrahydro-4,6-dioxo-pyrido[3,2-g]quinoline-2,8-dicarboxylic acid | 0.05 |
| 10-Fluoro-1,4,6,9-tetrahydro-4,6-dioxo-pyrido[3,2-g]quinoline-2,8-dicarboxylic acid | 0.10 |
| 1,4,6,9-Tetrahydro-4,6-dioxopyrido[3,2-g]-quinoline-2,8,10-tricarboxylic acid | 0.1 |
| 10-Chloro-1,4,6,9-tetraydro-4,6-dioxo-5-(trifluoromethyl)pyrido[3,2-g]quinoline-2,8-dicarboxylic acid | 0.5 |
| 10-Chloro-1,4,6,9-tetrahydro-5-methyl-4,6-dioxopyrido[3,2-g]quinoline-2,8-dicarboxylic acid | 0.01 |

Amine cations within the scope of the subject invention are pharmaceutically acceptable amine cations in the compounds of this invention. Amines previously exemplified earlier in the specification are suitable and preferred. Additional suitable amines include amines selected from the group consisting of $H_2NR'$, $HNR_2'$ and $NR_3'$, where $R'$ is selected from the group consisting of alkyl from one to three carbon atoms, and $-CH_2CH_2OH$.

Additional pharmaceutically acceptable metals include the alkaline earth metals such as calcium and magnesium and other metals such as aluminum.

Another sub genus of this invention are compounds where Z is hydrogen, R is selected from the group consisting of hydrogen and a pharmaceutically acceptable metal or amine cation, X is selected from the group consisting of cyano and $$\overset{O}{\underset{}{\overset{\|}{C}}}-OQ$$

where Q is selected from the group consisting of hydrogen and a pharmaceutically acceptable metal or amine cation and Q is the same as R; and Y is selected from the group consisting of hydrogen, alkyl from one to four carbon atoms, inclusive, halogen and alkoxy of from one to four carbon atoms, inclusive. A further sub genus of the invention are compounds where Z is hydrogen, R is selected from the group consisting of hydrogen and a pharmaceutically acceptable metal or amine cation, X is selected from the group consisting of hydrogen, alkyl from one to four carbon atoms, inclusive, halogen, and alkoxy of from one to four carbon atoms, inclusive, and Y is selected from the group consisting of cyano and $$\overset{O}{\underset{}{\overset{\|}{C}}}-OQ$$

where Q is selected from the group consisting of hydrogen and a pharmaceutically acceptable metal or amine cation and Q is the same as R.

We claim:
1. A compound of the formula wherein
R is selected from the group consisting of hydrogen, alkyl of one to three carbon atoms, inclusive, phenyl, and a pharmaceutically acceptable metal or amine cation;
X is selected from the group consisting of cyano and COOQ where Q is selected from the group consisting of hydrogen and a pharmaceutically acceptable metal or amine cation and when R is hydrogen or a pharmaceutically acceptable metal or amine cation, Q is the same as R; and
Y is selected from the group consisting of hydrogen, alkyl of one to four carbon atoms, inclusive; halogen and alkoxy of one to four carbon atoms, inclusive.

2. 1,4,6,9-Tetrahydro-4,6-dioxopyrido[3,2-g]quinoline-2,8,10-tricarboxylic acid according to claim 1.

3. 10-Cyano-1,4,6,9-tetrahydro-4,6-dioxopyrido[3,2-g]quinoline-2,8-dicarboxylic acid according to claim 1.

4. 5-Methyl-1,4,6,9-tetrahydro-4,6-dioxopyrido[3,2-g]quinoline-2,8,10-tricarboxylic acid according to claim 1.

5. 10-Cyano-1,4,6,9-tetrahydro-5-methyl-4,6-dioxopyrido[3,2-g]quinoline,2,8-dicarboxylic acid according to claim 1.

6. A compound in accordance with claim 1 wherein R is hydrogen or a pharmaceutically acceptable metal or amine cation.

* * * * *